United States Patent [19]

Marko et al.

[11] Patent Number: 4,956,486

[45] Date of Patent: Sep. 11, 1990

[54] REMOVAL OF ORGANIC CHLORIDE FROM PHENYLCHLOROSILANES

[75] Inventors: Ollie W. Marko; Robert D. Steinmeyer, both of Carrollton, Ky.

[73] Assignee: Dow Corning Corporation, Midland, Mich.

[21] Appl. No.: 489,631

[22] Filed: Mar. 7, 1990

[51] Int. Cl.$^5$ .............................................. C07F 7/20
[52] U.S. Cl. ................................................. 556/466
[58] Field of Search ...................................... 556/466

[56] References Cited

U.S. PATENT DOCUMENTS

| | | | |
|---|---|---|---|
| 3,168,542 | 2/1965 | Shaffer | 556/466 |
| 4,127,598 | 11/1978 | McEntee | 556/442 |
| 4,156,689 | 5/1979 | Ashby et al. | 556/466 X |
| 4,774,347 | 9/1988 | Marko et al. | 556/466 |
| 4,827,008 | 5/1989 | Gousetis et al. | 556/466 |

FOREIGN PATENT DOCUMENTS

| | | | |
|---|---|---|---|
| 50-39649 | 12/1975 | Japan | 556/466 |
| 0715581 | 2/1980 | U.S.S.R. | 556/466 |

*Primary Examiner*—Paul F. Shaver
*Attorney, Agent, or Firm*—William F. Boley

[57] ABSTRACT

The described invention is a process for reducing residual organic chlorides in a crude phenylchlorosilane mixture. The process involves contacting the organic chloride with a Lewis acid forming material, in the presence of a phenyl source. The phenyl source can be the phenylchlorosilanes and other sources of phenyl present in the crude phenylchlorosilane mixture. The organic portion of the organic chloride forms a hydrocarbon adduct with the phenyl source. If desired, the hydrocarbon adduct can be easily separated from the phenylchlorosilanes.

20 Claims, No Drawings

REMOVAL OF ORGANIC CHLORIDE FROM PHENYLCHLOROSILANES

BACKGROUND OF INVENTION

This invention relates to a process for reducing residual organic chloride species in phenylchlorosilanes. In the described process, a crude mixture comprising phenylchlorosilanes, organic chlorides, and a phenyl source are contacted with a Lewis acid forming material. The organic portion of the organic chlorides forms hydrocarbon adducts with the phenyl source. The hydrocarbon adducts can then be more easily separated from the phenylchlorosilanes.

Phenylchlorosilanes can be produced, for example, by a Grignard type reaction between chlorobenzene and methyltrichlorosilane methyltrichlorosilane. The result of this reaction is a crude mixture containing phenylchlorosilanes and a whole spectrum of chlorinated hydrocarbons and phenyl containing impurities. The organic chlorides, in many cases, have boiling points near those of the desired phenylchlorosilanes and can not be separated by the commonly used practice of distillation.

As impurities in the phenyhlchorosilanes, organic chlorides can serve as a latent sources of ionic chloride. This ionic chloride can create stability problems in hydrolysis intermediated formed from the phenylchlorosilanes. This problem has been found to exist even when the organic chlorides are present at parts per million in the phenylchlorosilane precursors to these hydrolysis intermediates. Therefore, a process which is effective at reducing organic chloride, even at these low levels, is desirable.

McEntee, U.S. Pat. No. 4,127,598, issued Nov. 28, 1978, describes a process for removing chlorinated biphenyls from impure phenylchlorosilanes with an adsorbent bed. The adsorbent bed is selected from a class consisting of a molecular sieve bed and a charcoal bed.

Motomiya, Japanese patent publication No. 50-39649, published Dec.18, 1975, describes a method for separating olefinic compounds and saturated compounds having a branching tertiary carbon from crude organohalosilanes. The described process is described as selectively polymerizing the hydrocarbon compounds when they are contacted with a Lewis acid or a metal hydroxide which can become a Lewis acid. The polymerized hydrocarbon compounds are separated from the organahalosilanes by distillation. The presence or removal of organic chlorides is not discussed by Motomiya.

Marko, et al., U.S. PAT. No. 4,774,347, issued Sept. 27, 1988, describes a process for reducing the chlorocarbon content of alkylsilanes. The described process comprises contacting crude alkylsilanes, containing as a minor portion chlorocarbons, and a hydrogen-containing silane with a catalyst. The catalyst is described as a Lewis acid forming material. In the described process, the chloride of the chlorocarbon is exchanged for a hydrogen atom of the hydrogen-containing silane to form a saturated hydrocarbon which may or may not be separated from the desired alkysilanes. This chemistry is not operative with the chlorine containing impurities found in phenylchlorosilanes.

SUMMARY OF INVENTION

A process for reducing residual organic chlorides in a crude phenylchlorosilane mixture is described. The process involves contacting the organic chloride with a Lewis acid forming material, in the presence of a phenyl source. The organic portion of the organic chloride forms a hydrocarbon adduct with the phenyl source. If desired, the hydrocarbon adduct can easily be separated from the phenylchlorosilane mixture.

DESCRIPTION OF INVENTION

The present invention is a process for reducing the organic chloride content of a crude mixture of phenylchlorosilanes under conditions described herein. The phenylchlorosilanes which can be reduced in organic chloride content by the described process have the formula:

$$\phi_a Me_b SiCl_{4-a-b};$$

where $a=1$, 2, or 3; $b=0$, 1, or 2,; $a+b=1,2$, or 3; $\phi$ is a phenyl radical; and Me is a methyl radical.

The process comprises:

(A) contacting a crude mixture containing as a major portion the phenylchlorosilanes and as a minor portions an organic chloride and a phenyl source, with a catalyst; where the catalyst is a Lewis acid forming material;

(B) facilitating contact of the organic chloride with the catalyst and the phenyl source to convert the organic chloride to hydrocarbon adducts;

(C) separating the catalyst from the phenylchlorosilanes and hydrocarbon adduct; and (D) recovering the phenylchlorosilanes with lowered organic chloride content.

The phenylchlorosilanes are part of a crude mixture. By crude mixture is meant, a mixture comprising at least a phenylchlorosilane, an organic chloride, and a phenyl source.

The phenylchlorosilane may be triphenylchlorosilane, diphenyldichlorosilane, phenyltrichlorosilane, methyldiphenylchlorosilane, dimethyphenylchlorosilane, and methylphenyldichlorosilane, alone or in combination in the crude mixture. The inventors have found the instant claimed process to be or particular benefit in removing the organic chloride, (2-chloroethyl)benzene, from crude mixtures containing as a major component methylphenyldichlorosilane. These two materials have boiling points within about 5° C. of each other and are typically very difficult to separate. For example, in the presence of toluene, the instant described process converts the (2-chloroethyl)benzene into the isomeric hydrocarbon adducts comprising 1-(o,p, or m)-tolyl-2-phenylethane and hydrogen chloride. These hydrocarbon adducts and resultant hydrogen chloride can easily be separated from the desired phenylchlorosilanes by distillation.

The phenyl source can be benzene or any compound substituted with one or more phenyl radicals capable of reacting with a carbonium ion, for example, toluene. A preferred embodiment of the instant process is when the crude mixture is the result of a Grignard process to prepare phenylchlorosilanes. In this situation, the addition of a phenyl source is not necessary, since phenyl containing impurities in the mixture can serve as an inherent source of phenyl. Optionally, a phenyl source can be added to the crude mixture as a supplemental source of phenyl. The phenylchlorosilanes may also serve as a phenyl source.

For the purposes of the instant invention, the term "Lewis acid forming material" means, that the catalysts that have been found effective in facilitating the reaction of an organic chloride with a phenyl source have all been Lewis acid forming materials. It is theorized that Lewis acid forming materials are generally effective as catalyst. However, due to differences in physical characteristics the catalytic activity of the Lewis acid may not follow the classic order of Lewis acid strengths. The Lewis acid forming materials can be, for example, alumnia, silicaalumina mixtures, zeolites, aluminum chloride, cobalt chloride, ferric chloride, copper chloride, stannous chloride, palladium chloride and zirconium chloride. Zeolites are such materials as aluminum and calcium or sodium silicates. The preferred Lewis acid forming materials are alumina, silica-alumina mixtures, and zeolites.

The catalyst contacts the crude mixture as a solid. The catalyst can be in a form, for example, such as powders, granules, pellets, tablets, lumps, or extrudates.

It is theorized, by the inventors, that the procress relies on a Lewis acid catalyzed Friedel-Crafts alkylation reaction between the organic chloride and any available phenyl source in the crude mixture. Therefore, any organic chloride capable of reacting with the Lewis acid forming material to form a carbonium ion of structure $R_3C+$, where R is hydrogen or a hydrocarbon radical, can be converted to a non-chlorine containing hydrocarbon adduct by substitution of the carbonium ion forming material into the phenyl ring of the phenyl source. Preferred organic chlorides are those capable of forming a carbonium ion of structure $RCH_2+$, where R is a hydrocarbon radical. The hydrocarbon radical(s) can be, for example, alkyl, alkenyl, aryl, and alkylaryl. The organic chlorides which can be converted to hydrocarbon adducts can be, for example, (2-chloroethyl)-benzene, ethyl chloride, 2-chloropropane, and benzyl chloride.

Contacting the catalyst with the crude mixture containing the phenylchlorosilanes, phenyl source, and organic chlorides can be effected in either a batch or continuous mode. In a batch mode, liquid crude mixture and a solid catalyst can be contacted by such conventional means as a stirred-tank reactor. Contacting the crude mixture and solid catalyst can be effected in a continuous mode by such conventional means as a packed-bed reactor or a stirred-tank reactor with continuous feed and continuous product takeoff. Contact of the crude mixture with the catalyst in a packed-bed in a continuous mode is a preferred embodiment.

"Facilitating reaction of the organic chloride with the catalyst and the phenyl source" means, for the purpose of the instant invention, providing a temperature controlled environment for contact of the crude mixture with the solid catalyst. In addition, such facilities as feed systems for the crude mixture; and adequate agitation to assure sufficient contact of the liquid reactants with the solid catalyst in a stirred tank reactor may be provided.

Catalyst concentration, relative to the organic chloride concentration of the crude mixture, is not critical to the operation of the instant invention. However, catalyst concentration will affect the length of time required to achieve the desired reduction in organic chloride content and the amount of organic chloride reduction. Thus, a packed column in which the reactants contact a large surface area of catalyst in a short period of time is preferred.

The effectiveness of removal of organic chlorides by the instant process is a function of both the temperature at which the organic chlorides are contacted with the catalyst and the length of time of the contact. In general, a contact temperature of 75° C. to 200° C. has been found to be useful. At temperature below 75° C., required contact times become long and effectiveness of organic chloride removal is significantly reduced. At temperatures above 200° C., phenyl cleavage can occur. A preferred contact temperature is 120° C. to 180° C. Most preferred, is a contact temperatute of about 140° C.

The contact time required to remove the organic chloride from the crude mixture will depend upon the contact temperature. In general, the higher the contact temperature the shorter the required contact time. A useful contact time for the organic chloride with the catalyst is about one minute to two hours. A preferred range for the contact time is five minutes to one hour. Most preferred is a contact time of about 30 minutes when the contact temperature is about 140° C.

Separating the catalyst from the phenylchlorosilanes and hydrocarbon adducts can be effected by conventional means. When the process is operated in a batch mode or a continuous mode in a stirred-tank reactor, the total catalyst charge can be separated by such means as a settling tank, filtration, or a combination thereof. When a packed bed of catalyst is used in a continuous mode, the bulk of the catalyst will be retained in the bed. Any catalyst fines not held in the packed bed can be removed by conventional settling or filtration.

Once catalyst solids are separated from the liquid, the liquid product may be used directly. In many cases, the content of the resulting hydrocarbon adducts from the reaction of organic chlorides with the phenyl source is very low and a particular use for the purified phenylchlorosilanes may not necessitate isolation and separation of the hydrocarbon adducts. Therefore, recovering phenylchlorosilanes with lower organic chloride content may encompass nothing more than appropriate containment procedures. However, where quality requirements dictate that the hydrocarbon adducts be removed, the process can further comprise separating the phenylchlorosilanes from the hydrocarbon adducts. A preferred means for separating the phenylchlorosilanes from the hydrocarbon adducts is distillation.

So that those skilled in the art may better understand and appreciate the instant invention, the following examples are presented. These examples are presented to be illustrative and are not to be construed as limiting the invention as claimed herein.

Example 1. (Not within the scope of the present invention) An attempt was made to remove an organic chloride from methylphenyldichlorosilane by a process similar to that described in Marko et al., U.S. Pat. No. 4,774,347, issued Sept. 27, 1988.

An apparatus was assembled that consisted of a liquid feed reservoir, a positive-displacement metering pump, pressure regular, and a ½-inch diameter by 18-inch stainless tube. The temperature of the tube and its contents was controlled by immersing the tube into a constant temperature, circulating oil bath, the bath having a temperature control device. The outlet of the reaction tube was fitted so that effluent samples could be taken for analysis. Analyses were carried out using gas chromatography (GC) and GC with a mass spectrometer detector (GC/MS).

A sample of methylphenyldichlorosilane to which had been added one percent (2-chloroethyl)benzene, two percent toluene, and one percent dimethylchlorosilane was passed through the pressurized reactor column packed with alumina, United Catalysts, Inc. All percentages are based on weight to total weight proportions. For one sample, the residence time within the column was five minutes and the column temperature was 30° C. A second similar sample was passed through an alumina filled column with a two minute residence time and a column temperature of 60° C. Eluates from the columns were analyzed by GC and GC/MS. In neither case, was the expected reaction product, ethylbenzene, observed. None of the (2-chloroethyl)benzene was consumed.

This data demonstrates that under these conditions, organic chlorides, such as (2-chloroethyl)benzene, are not removed from phenylchlorosilanes by the chloride-hydride exchange process of Marko et al., supra.

Example 2. A designed experiment was ran to evaluate the removal of organic chlorides from phenylchlorosilanes, in the presence of a phenyl source and a Lewis acid catalyst. The apparatus employed was the same as that used in Example 1.

Undistilled methylphenyldichlorosilane, prepared by a Grignard process, containing 14, 181 ppm (2-chloroethyl) benzene was passed through an alumina packed column. The residence time (RT) and column temperature (Col. Temp.) for each run are presented in Table 1. The eludate from the column was analyzed by GC and GC/MS for (2-chloroethyl) benzene (2-CEBz). The percent 2-CEBz removed is presented in Table 1.

TABLE 1.

Removal of 2-CEBz From Methylphenyldichlorosilane

| Col. Temp. (°C.) | RT (Min.) | % 2-CEBz Removed |
|---|---|---|
| 100 | 30 | 64 |
| 120 | 30 | 96 |
| 120 | 15 | 87 |
| 120 | 5 | 70 |
| 140 | 30 | 99 |
| 140 | 15 | 89 |

The data indicate that a 30 minute resident time at a column temperature of 140° C. quantitatively removed 2-CEBz. The GC/MS analysis demonstrated that a series of nonchloride containing Friedel-Crafts alkylation products were formed by reaction of the (2-chloroethyl)benzene with other phenyl sources in the feed stock.

What is claimed is

1. A process for reducing organic chloride content of phenylchlorosilanes, where the phenylchlorosilanes are of formula

$\phi_a Me_b SiCl_{4-a-b}$;

where a=1, 2, or 3; b=0, 1, or 2,; a+b=1, 2, or 3; $\phi$ is a phenyl radical; and Me is a methyl radical;
the process comprising:

(A) contacting a crude mixture containing as a major portion the phenylchlorosilanes and as minor portions an organic chloride and a phenyl source, with a catalyst; where the catalyst is a Lewis acid forming material;

(B) facilitating contact of the organic chloride with the catalyst and the phenyl source to convert the organic chloride to hydrocarbon adducts;

(C) separating the catalyst from the phenylchlorosilanes and the hydrocarbon adducts; and (D) recovering the phenylchlorosilanes with lowered organic chloride content.

2. A process according to claim 1, where the catalyst is selected from a group consisting of alumina, silicaalumina mixtures, zeolites, aluminum chloride, cobalt chloride, ferric chloride, copper chloride, stannuous chloride, palladium chloride, and zirconium chloride.

3. A process according to claim 1, where the catalyst is selected from a group consisting of alumina, silicaalumina mixtures, and zeolites.

4. A process according to claim 1, where contacting the crude mixture with the catalyst is effected at a contact temperature of 75° C. to 200° C.

5. A process according to claim 4, where the contact temperature is 120° C. to 180° C.

6. A process according to claim 4, where the crude mixture is contacted with the catalyst for a contact time of one minute to two hours.

7. A process according to claim 5, where the crude mixture is contacted with the catalyst for a contact time of five minutes to one hour.

8. A process according to claim 1, where contacting the crude mixture with the catalyst is effected in a packed bed in a continuous mode.

9. A process according to claim 8, where the catalyst is selected from a group consisting of alumina, silicaalumina mixtures, and zeolites.

10. A process according to claim 9, where the crude mixture is contacted with the catalyst for a contact time of five minutes to one hour and at a contact temperature of 120° C. to 180° C.

11. A process according to claim 9, where the crude mixture contains as the major portion methylphenyldichlorosilane and as a minor portion (2-chloroethyl)benzene.

12. A process according to claim 11, where the crude mixture is contacted with alumnia at a contact temperature of about 140° C. for a contact time of about 30 minutes.

13. A process for reducing organic chloride content of phenylchlorosilanes, where the phenylchlorosilanes are of formula

$\phi_a Me_b SiCl_{4-a-b}$;

where a=1, 2, or 3; b=0, 1, or 2,; a+b=1, 2, or 3; $\phi$ is a phenyl radical; and Me is a methyl radical;
the process comprising:

(A) contacting a crude mixture containing as a major portion the phenylchlorosilanes and as a minor portion an organic chloride, with a catalyst; where the catalyst is a Lewis acid forming material; p1 (B) facilitating contact of the organic chloride with the catalyst and the phenylchlorosilane to convert the organic chloride to hydrocarbon adducts;

(C) separating the catalyst from the phenylchlorosilanes and the hydrocarbon adducts; and p1 (D) recovering the phenylchlorosilanes with lowered organic chloride content.

14. A process according to claim 13, where the catalyst is selected from a group consisting of alumina, silica-alumina mixtures, zeolites, aluminum chloride, cobalt chloride, palladium chloride, and zirconium chloride.

15. A process according to claim 13, where the catalyst is selected from a group consisting of alumina, silica-alumina mixtures, and zeolites.

16. A process according to claim 15, where contacting the crude mixture with the catalyst is effected in a packed bed in a continuous mode.

17. A procedss according to claim 16, where the crude mixture is contracted with the catalyst for a contact time of five minutes to one hour and at a contact temperature of 120° C. to 180° C.

18. A process according to claim 13, where the crude mixture contains as the major portion methylphenyldichlorosilane and as a minor portion (2-chloroethyl)benzene.

19. A process according to claim 18, where the crude mixture is contacted with alumina at a contact temperature of about 140° C. for a contact time of about 30 minutes.

20. A process according to claim 1, where recovering the phenylchlorosilanes with lowered organic chloride content is effected by distillation.

* * * * *